United States Patent [19]

Holloway et al.

[11] Patent Number: 4,927,836

[45] Date of Patent: May 22, 1990

[54] AMIDE DERIVATIVES

[75] Inventors: Brian R. Holloway, Congleton; Ralph Howe, MacClesfield; Balbir S. Rao, Holmes Chapel; Donald Stribling, Prestbury, all of England

[73] Assignee: Imperial Chemical Industries PLC, London, England

[21] Appl. No.: 213,259

[22] Filed: Jun. 29, 1988

Related U.S. Application Data

[63] Continuation-in-part of Ser. No. 75,983, Jul. 21, 1987, abandoned.

[30] Foreign Application Priority Data

Jul. 23, 1986 [GB] United Kingdom ............... 8617986
Jan. 28, 1987 [GB] United Kingdom ............... 8701832

[51] Int. Cl.$^5$ ............... A61K 31/16; A61K 31/165; C07C 103/20
[52] U.S. Cl. ............................ 514/620; 564/157; 564/165; 514/211; 514/212; 514/213; 514/224.2; 514/226.8; 514/227.5; 514/230.5; 514/237.8; 514/307; 514/311; 514/317; 514/331; 514/365; 514/367; 514/374; 514/375; 514/415; 514/416; 514/522; 514/616; 540/450; 540/467; 540/544; 540/607; 544/58.5; 544/162; 546/196; 546/226; 548/540; 558/414
[58] Field of Search ......................... 564/165; 514/620

[56] References Cited

U.S. PATENT DOCUMENTS 4,263,323 4/1981 Carlsson et al. ............... 564/165
4,460,580 7/1984 Ostermayer et al. ............ 564/165
4,478,849 10/1984 Ainsworth et al. ............. 564/165

FOREIGN PATENT DOCUMENTS 0171760 7/1986 European Pat. Off. ......... 564/165
2101119 1/1983 United Kingdom ............ 564/165

OTHER PUBLICATIONS

Duckworth et al., "Substituted (phenoxypropylaminoethoxyphenoxy)acetamides", CA, 104, 224722r, Jun. 23, 1986.

Primary Examiner—Glennon H. Hollrah
Assistant Examiner—Susan P. Treanor
Attorney, Agent, or Firm—Cushman, Darby & Cushman

[57] ABSTRACT

The invention concerns novel phenoxyacetic acid amide derivatives of the formula I (and pharmaceutically acceptable salts thereof) in which $R^1$ is hydrogen or fluoro, $R^2$ is phenyl, cycloalkyl, alkyl or alkenyl as defined herein, and $R^3$ is hydrogen, methyl or ethyl, or $R^2$ and $R^3$ together form polymethylene as defined herein. The invention also includes pharmaceutical compositions containing the amide derivatives, means for the manufacture of the said derivatives and for their use in the treatment of obesity and related conditions and/or in the manufacture of novel medicaments.

14 Claims, No Drawings

AMIDE DERIVATIVES

This application is a continuation-in-part of application Ser. No. 075,983, filed July 21, 1987, now abandoned.

This invention concerns novel amide derivatives and, more particularly, novel phenoxyacetic acid amide derivatives containing a (2-hydroxy-3-phenoxypropyl)amino group, which amides stimulate thermogenesis in warm-blooded animals and are of use, for example, in the treatment of obesity and related conditions, such as obesity of mature onset diabetes. The invention also provides pharmaceutical compositions for use in the administration of the amide derivatives of the invention to warm-blooded animals, processes for the manufacture of the said derivatives, and the use of the said derivatives in the treatment of (and/or manufacture of thermogenic medicaments for use in the treatment of) obesity and related conditions.

In European patent application, publication no 171760 there is described a series of phenolic phenoxyacetic acid amide derivatives which are said to be ionotropic agents of value in treating congestive heart disease. We have now discovered (and this is a basis for the the present invention) that, surprisingly, certain novel amide derivatives of the formula I defined below, which differ from the compounds of the art in lacking a phenolic hydroxy group, possess significant thermogenic properties at doses which cause relatively little cardiac stimulation, it being understood that selectivity of thermogenic effect is an important requirement for a useful agent in the treatment of, for example, obesity and related conditions.

According to the invention there is provided an amide derivative of the formula I [set out hereinafter together with the other chemical formulae identified by Roman numerals] wherein $R^1$ is hydrogen or fluoro; $R^2$ is phenyl optionally bearing a halogeno, (1–4C)alkyl, (1–4C)alkoxy, trifluoromethyl, cyano or nitro substituent, (3–6C)cycloalkyl, (1–4C)alkyl in which the carbon atom linked to the nitrogen of $NR^2R^3$ bears one or two hydrogens, or $R^2$ is (3–4C)alkenyl, either of which latter groups may optionally bear a hydroxy, carbamoyl, (1–4C)alkoxy, phenyl or chlorophenyl substituent; and $R^3$ is hydrogen, methyl or ethyl; or $R^2$ and $R^3$ together form (4–7C)polymethylene, in which one methylene unit may optionally be replaced by oxygen or sulphur situated at least 2 carbon atoms distant from the nitrogen atom of $NR^2R^3$, and in which two adjacent methylene units may optionally be replaced by 2 carbon atoms of a benzene ring fused to said (4–7C)polymethylene, said benzene ring itself optionally bearing a halogeno, (1–4C)alkoxy, (1–4C)alkyl, trifluoromethyl, cyano or nitro substituent; or a pharmaceutically acceptable acid-addition salt thereof.

It will be appreciated that the compounds of formula I contain one or more asymmetric carbon atoms and can exist as optically active enantiomers or as optically inactive racemates. The present invention encompasses any enantiomer, racemate and/or (when two or more asymmetric carbon atoms are present) diastereoisomer, which possesses thermogenic properties in warm-blooded animals, it being well known in the chemical art how to prepare individual enantiomers, for example by resolution of the racemate or by stereospecific synthesis, and how to determine the thermogenic properties, for example, using the standard tests described hereinafter.

The group $-OCH_2CO.NR^2R^3$ is generally located in the meta- or para-position relative to the oxyethylamino side-chain, of which positions the paraposition is preferred.

A preferred value for $R^1$ is hydrogen.

A particular value for $R^2$ when it is (1–4C)alkyl or (3–4C)alkenyl as defined above is, for example, methyl, ethyl, propyl, isopropyl, butyl, isobutyl, allyl or 2-methyl-2-propenyl, optionally bearing a substituent selected from hydroxy, carbamoyl, (1–4C)alkoxy (such as methoxy or ethoxy), phenyl and chlorophenyl (in particular, p-chlorophenyl).

A particular value for $R^2$ when it is phenyl is, for example, unsubstituted phenyl or phenyl bearing a substituent selected from fluoro, chloro, bromo, methoxy, ethoxy, methyl, ethyl, trifluoromethyl, cyano and nitro.

A particular value for $R^2$ when it is (3–6C)cycloalkyl is, for example cyclobutyl, cyclopentyl or cyclohexyl.

Specific values for optional substituents which may be present when $R^2$ is phenyl, or when a part of $R^2$ and $R^3$ together is a benzene moiety, as defined above, include for example:

for halogeno: fluoro, chloro and bromo;
for (1–4C)alkoxy: methoxy, ethoxy, propoxy and isopropoxy; and
for (1–4C)alkyl: methyl, ethyl, propyl, isopropyl and t-butyl.

A preferred value for $R^3$ is, for example, hydrogen.

A particular value for $R^2$ and $R^3$ when together they form (4–7C)polymethylene is, for example, tetramethylene or pentamethylene, and when together they form (4–7C)polymethylene in which one methylene unit is replaced by oxygen or sulphur is, for example, ethyleneoxyethylene or ethylenethioethylene.

Specific values for the group $-NR^2R^3$ include, for example, anilino, benzylamino, allylamino, cyclohexylamino, cyclopentylamino, morpholino, piperidino, pyrrolidino, dimethylamino, diethylamino, methylamino, ethylamino, propylamino, isopropylamino, butylamino, isobutylamino, (2-hydroxyethyl)amino, (3-hydroxypropyl)amino, (2-methoxyethyl)amino, indolinl-yl, 1,2,3,4-tetrahydroisoquinol-2-yl and 1,2,3,4-tetrahydroquinol-1-yl.

A preferred group of compounds of the invention comprises those compounds of formula I wherein $R^1$ is hydrogen; the group $NR^2R^3$ is (1–4C)alkylamino (in which (1–4C)alkyl is as defined hereinbefore) (and especially methylamino or ethylamino), benzylamino, piperidino, pyrrolidino, (3–4C)alkenylamino, morpholino or 1,2,3,4-tetrahydroisoquinol2-yl; and the groups $-OCH_2.CO.NR^2R^3$ and $-O.CH_2CH_2.NH-$ are attached in pararelationship; together with the pharmaceutically acceptable acid-addition salts thereof.

A further preferred group of compounds comprises those compounds of formula I wherein $R^1$ is hydrogen; the group $-NR^2R^3$ is methylamino, ethylamino, propylamino, isopropylamino, (2-hydroxyethyl)amino, (3-hydroxypropyl)amino, (2-methoxyethyl)amino, (3-methoxypropylamino or 1,2,3,4-tetrahydroisoquinol2-yl; and the groups $-OCH_2.CO.NR^2R^3$ and $-O.CH_2CH_2.NH-$ are attached in pararelationship; together with the pharmaceutically acceptable acid-addition salts thereof.

Typical compounds of formula I are set out in the accompanying Examples. Compounds of particular interest are those of Examples 1, 2, 5, 7, 16, 19 and 21, which are provided, together with their pharmaceutically acceptable acidaddition salts, as a further feature of the invention.

The compounds of formula I are basic and may be isolated and used either in the form of the free base or of a pharmaceutically acceptable acid-addition salt thereof. Particular examples of pharmaceutically acceptable acid-addition salts include, for example, salts with inorganic acids such as hydrohalides (especially hydrochlorides or hydrobromides), sulphates and phosphates, and salts with organic acids such as succinates, citrates, lactates, tartrates, oxalates and salts derived from acidic polymeric resins, such as the free acid form of sulphonated polystyrene.

The novel compounds of formula I may be obtained by conventional processes of organic chemistry well known in the art for the production of structurally analogous compounds, for example as set out in our UK patent specification, Ser. No. 1,455,116. Such processes are provided as a further feature of the invention and are illustrated by the following procedures in which $R^1$, $R^2$ and $R^3$ have any of the meanings previously defined:

(a) An ester of the formula II wherein $R^4$ is (1–6C)alkoxy, phenoxy or benzyloxy, is reacted with an amine of the formula $HNR^2R^3$.

A particularly suitable value for $R^4$ is, for example, methoxy or ethoxy.

The process is generally performed in a suitable inert solvent or diluent, for example, a (1–4C)alkanol such as methanol or ethanol, and at a temperature in the range, for example, 0° to 60°, optionally in a pressure vessel when a volatile amine such as methylamine is used. The amine of the formula $HNR^2R^3$ is conveniently present as an excess.

The necessary starting esters may be obtained by reacting a phenol derivative of the formula III with an alkylating agent of the formula $X.CH_2.CO.R^4$ wherein X is a suitable leaving group, for example, chloro, bromo or iodo, and $R^4$ has the meaning given above, in the presence of a base, for example as described in the accompanying Examples. It will be appreciated that this procedure is analogous to the process (b) below and that generally similar reaction conditions and bases may be employed.

(b) A phenol derivative of the formula III is reacted with an alkylating agent of the formula $X.CH_2.CO.NR^2R^3$ wherein X is a suitable leaving group, for example a chloro, bromo, iodo, methanesulphonyloxy or p-toluenesulphonyloxy group.

The process is conveniently performed in the presence of an external base, for example an inorganic base such as an alkali metal carbonate or acetate (e.g. potassium carbonate or sodium acetate), or an alkali metal hydride (e.g. sodium hydride), and at a temperature in the range, for example, 10° to 120° C. A suitable solvent or diluent, for example acetone, methyl ethyl ketone, propan-2-ol, 1,2-dimethoxyethane or t-butyl methyl ether may conveniently be used. In order to minimise side-reactions, the process may also be carried out by pre-reacting the phenol of formula III with a suitable base to form the corresponding salt which is then added to the alkylating agent of the formula $X.CH_2.CO.NR^2R^3$.

The starting phenol derivatives of formula III may be obtained by conventional procedures of organic chemistry. Thus, for example, they may be obtained by reaction of a phenol of the formula IV with an epoxide of the formula V in a suitable solvent or diluent, for example, an alcohol such as ethanol or propan-2-ol, at a temperature in the range, for example, 10° to 110° C. and conveniently at or near the boiling point of the reaction mixture. The epoxides of formula V are known per se but can be made by reaction of phenol or o-fluorophenol with epichlorohydrin or epibromohydrin in the presence of a suitable base such as an alkali metal hydroxide, piperidine, morpholine or N-methylmorpholine, in a suitable solvent or diluent such as methanol, ethanol or propan-2-ol, conveniently at or near the boiling point of the reaction mixture.

In general, it is preferred to react the epoxide of formula V with a protected phenol derivative of formula VI wherein Q is a suitable protecting group, such as benzyl. In this case, following the reaction of compounds V and VI, the protecting group is removed, for example in the case of benzyl by hydrogenolysis, for example using hydrogenation at a pressure in the range, for example, 3 to 30 bar in the presence of a palladium-on-carbon catalyst in an inert diluent or solvent for example, a (1–4C)alkanol (such as methanol, ethanol or t-butyl alcohol) or a (1–4C)alkanoic acid (such as acetic acid) and at a temperature of, for example, 20°–80° C.

It is to be understood that the epoxides of formulae V may be used in their racemic or enantiomeric forms.

(c) An amine derivative of the formula VII is reacted with an epoxide of formula V.

It will be appreciated that this reaction is a modification of the procedure described above for the production of the starting materials of formula III and that, therefore, generally similar reaction conditions may be employed.

The starting amine derivatives of formula VII may be made from the corresponding phenols of formula IV by reaction with a compound of the formula $X.CH_2.CONR^2R^3$ as defined above using analogous reaction conditions to those described above in process (b).

(d) A protected derivative of the formula VIII wherein Q is a suitable protecting group is deprotected.

A suitable protecting group is, for example, a hydrogenolysable group such as benzyl, 4-methoxybenzyl or 3,4-dimethoxybenzyl, which may be removed, for example by hydrogenation using conditions similar to those defined above in the production of the starting materials for process (b). Hydrogen pressure of, for example, 3 to 30 bar may be used at a temperature in the general range, for example, 20° to 80° C.

The protected derivatives of formula VIII may be obtained by using process (b) or (c) with appropriate starting materials in which the amino group is protected with a suitable protecting group. When Q is benzyl, the corresponding benzylated starting materials analogous to those of formula VII may conveniently be obtained, for example, by reductive alkylation of the compounds of formula VII with benzaldehyde in the presence of sodium borohydride in a solvent or diluent such as methanol at 0° to 25° C.

Whereafter, when a pharmaceutically acceptable acid-addition salt is required, the compound of formula I in free base form is reacted with the appropriate acid using a conventional procedure. For example, when a hydrogen halide salt is required, it may conveniently be obtained by hydrogenation of the free base together with the stoichiometric amount of the corresponding benzyl halide.

Whereafter, when an enantiomer is required, the corresponding racemate may be resolved, for example by reaction with a suitable optically active acid using a conventional procedure. Alternatively, one of the above processes may be carried out using an optically active starting material.

As stated above, the compounds of formula I possess thermogenic properties and are of use in the treatment of obesity and/or related diseases of metabolic dysfunction, such as diabetes mellitus especially of adult onset. In addition, in some cases, the compounds of formula I may be of value in modification of carcass composition, for example, by increased catabolism of fat in meat producing animals, such as cattle, pigs, sheep, goats and/or rabbits.

The thermogenic effects of compounds of formula I may be demonstrated using one or more of the following standard tests:

(a) Rats are cold adapted by being placed in a cold environment (4° C.) for 10 days in order to increase their capacity for thermogenesis. They are then transferred to a thermoneutral environment (29° C.). Three hours later the core temperature is measured to determine a base-line reading and the test compound is administered subcutaneously or orally as a solution or suspension in 0.45% w/v aqueous sodium chloride, 0.25% w/v Polysorbate 80. After one hour, the core temperature is again measured. In this test, a compound which causes a statistically significant increase in the core temperature of about 0.3° C. (or more) at a sub-cutaneous dose of 15 mg/kg (or less) is considered to be significantly active. The test acts as a model for the depressed thermogenesis which occurs during dieting.

(b) Rats are cold adapted at 4° C. for 4 days to increase their capacity for thermogenesis. They are then transferred to a warm environment of 23° C. for 2 days. On the following day, a test compound is administered subcutaneously or orally as described in (a). Animals are sacrificed one hour later and the interscapular, brown adipose tissue (BAT) pad is removed. BAT mitochondria are prepared by differential centrifugation and GDP binding is determined (Holloway et al., *International Journal of Obesity*, 1984, 8, 295) as a measure of thermogenic activation. Each test includes a control which is dosed with the solution/suspension vehicle only and a positive control which is dosed with isoprenaline (as its sulphate) at 1 mg/kg. Test compounds are routinely dosed at 0.1, 0.3, 1.0, 3.0, and 10 mg/kg and results expressed in terms of the effect on GDP binding produced by isoprenaline. From these results, a dose ($ED_{50}$) necessary to produce 50% of the isoprenaline effect is calculated by linear regression analysis. Compounds are considered active in this test if they cause a significant elevation in GDP binding as compared to controls. This test serves to indicate that the thermogenic effects observed in test (a) are mediated through an increase in effect on BAT rather than by some non-specific or toxic mechanism.

(c) Rats are adapted to a thermoneutral environment (29° C.) for 2 weeks in order to decrease their capacity for BAT mediated non-shivering thermogenesis. During the final 3 days the animals are trained to use an apparatus for measuring heart rate non-invasively via foot-pad electrodes connected to an ECG integrator giving a continuous read-out of heart rate. A test compound is administered sub-cutaneously at the $ED_{50}$ determined in test (b), and heart rate is determined 15–30 minutes after dosing. The procedure is then repeated in subsequent tests using increasing multiples of the $ED_{50}$ determined in test (b) until the heart rate (HR) reaches or exceeds 500 beats per minute, allowing the dose necessary to produce a heart rate of 500 beats per minute ($D_{500}$ dose) to be calculated.

The ratio of $D_{500}$ to $ED_{50}$ in test (b) can be defined as the selectivity index (SI) and provides a measure of the selectivity of the compound for BAT as opposed to the cardiovascular system. Compounds are considered to have significant selectivity which have an SI of $>1$. Non-selective compounds have an SI of $<1$ (for example isoprenaline=0.06).

(d) Rats are cold adapted at 4° C. for four days to increase their capacity for thermogenesis. They are then transferred to a warm environment at 23° C. for two days. On the following day, the basal metabolic rate of the animals is determined using a close-circuit oxygen consumption apparatus of the type described by Arundel et al., 1984, *J. Appl. Physiol. Respirat. Environ. Exercise Physiol.*, 1984, 57 (5) 1591–1593. The rats are then dosed (orally or sub-cutaneously) with test compound at about (10 mg/kg) as a solution or suspension in 0.45% w/v aqueous sodium chloride, 0.25% w/v Polysorbate 80. Metabolic rate is then determined for at least one hour after dosing. Compounds are considered active in this test if they cause a significant increase in metabolic rate as compared to control animals (Student's t test: p $<0.5$) dosed only the solution or suspension vehicle.

In the above tests, the compounds of formula I in general produce effects of the following order without producing overt toxicity:

test (a): increase in core temperature of about 0.5° C. (or more) following a sub-cutaneous dosage of $<15$ mg/kg;

test (b): sub-cutaneous $ED_{50}$ for GDP binding in BAT mitochondria of 0.01–10 mg/kg; and test (c): show an SI of $<50$.

By way of illustration, the compound described in the accompanying Example 1, produced the following effects in the above tests:

(a) 2.25° C. at a sub-cutaneous dose of 10 mg/kg;

(b) sub-cutaneous $ED_{50}$: 0.133 mg/kg; oral $ED_{50}$ 1.18 mg/kg;

(c) $D_{500}$: $>13.3$ mg/kg (sub-cut.); SI $>100$ (sub-cut.); SI $>50$ (oral).

By contrast, the known, structurally related compound N-methyl-2-p-(2-[(2-hydroxy-3-[p-hydroxyphenoxy] propyl)amino]ethoxy)phenoxyacetamide, described in Example 2 of European patent application, publication no. 171760, produced a temperature rise of 1.24° C. in test (a) and no significant activity in test (b), but produced a marked increase in heart rate.

When used to produce thermogenic effects in warm-blooded animals including man, a compound of formula I, or a pharmaceutically acceptable salt thereof as appropriate, will be administered so that a dose in the general range 0.002–20 mg/kg, and preferably in the range 0.02–10 mg/kg, is administered daily, given in a single dose or divided doses as necessary. However, it will be appreciated by those skilled in the art that dosage will necessarily be varied as appropriate, depending on the severity of the condition under treatment and on the age and sex of the patient and according to known medical principles.

The compounds of formula I will generally be used for medical (or veterinary) purposes in the form of compositions comprising a compound of formula I, or a pharmaceutically (or veterinarily) acceptable salt thereof as appropriate, as the active ingredient together with a pharmaceutically (or veterinarily) acceptable diluent or carrier. Such compositions are included in the invention and will typically be adapted for oral administration (including tablets, capsules, pills, powders, solutions, suspensions and the like) or parenteral administration (including sterile solutions, suspensions and emulsions).

Compositions adapted for oral administration are generally preferred.

The compositions may be obtained using standard excipients and procedures well known in the art. A unit dose form such as a tablet or capsule will usually contain, for example 0.1–250 mg of active ingredient. The compositions may also contain other active ingredients known for use in the treatment of obesity and related conditions, for example appetite suppressants, vitamins and hypoglycaemic agents.

The invention will now be illustrated by the following Examples in which, unless otherwise stated:

(a) all operations were carried out at room temperature that is at a temperature in the range 18°–26° C.;

(b) evaporations were performed under reduced pressure on a rotary evaporator;

(c) chromatography was carried out on Merck Kieselgel (Art 7734) obtainable from E. Merck, Darmstadt, Federal Republic of Germany;

(d) yields are for illustration only and are not to be interpreted as the maximum attainable by diligent process development;

(e) nuclear magnetic resonance (NMR) spectra were determined at 200 MHz in $d_6$-DMSO as solvent using tetramethylsilane (TMS) an internal standard and are expressed in delta values (parts per million) for protons relative to TMS, using conventional abbreviations to describe signal types; and (f) all crystalline end-products had satisfactory microanalyses and NMR spectra.

EXAMPLE 1

A mixture of methyl 2-p-(2-[(2-hydroxy-3-phenoxypropyl)-amino]ethoxy)phenoxyacetate (0.38 g) in methanol (20 ml) and a 33% w/v solution of methylamine in ethanol (10 ml) was allowed to stand at ambient temperature for 3 hours. The solvent was evaporated and the residue was crystallised from ethyl acetate to give N-methyl-2-p-(2-[(2-hydroxy-3-phenoxypropyl)amino]ethoxy)phenoxyacetamide (0.24 g), mp 115° C.; microanalysis: found C,63.9; H,7.0; N,7.3%; required for $C_{20}H_{26}N_2O_5$: C,64.2; H,7.0; N,7.5%; NMR: 1.84 (br s, 1H, NH); 2.68 (m, 5H, CH(OH).C$\underline{H}_2$NH+NHC$\underline{H}_3$); 2.86 (t,2H, NHC$\underline{H}_2$CH$_2$O); 3.90 (m, 5H, OC$\underline{H}_2$C$\underline{H}$(OH)+OC$\underline{H}_2$C$\underline{H}_2$); 4.38 (s, 2H, OCH$_2$.CO); 4.80 (br s, 1H, OH); 6.80–7.00 (m, 7 aromatic H); 7.25 (m, 2 aromatic H); 7.80 (br s, 1H, CO.NH).

The starting material was obtained as follows:

A mixture of N-benzyl-N-(2-p-hydroxyphenoxyethyl)-2-hydroxy-3-phenoxypropylamine (4.0 g), methyl bromoacetate (1.56 g), anhydrous potassium carbonate (1.7 g) and potassium iodide (0.05 g) was stirred under reflux in dry acetone (50 ml) for 24 hours.

The reaction mixture was cooled, solid removed by filtration and solvent evaporated. The residue of methyl 2-p-(2-[N-benzyl-(2-hydroxy-3-phenoxypropyl)-amino]ethoxy)phenoxyacetate was dissolved in methanol (90 ml) and acetic acid (30 ml). The solution obtained was hydrogenated in the presence of 10% w/w palladium-on-carbon (0.4 g) at about 20 bar and 60° C. for 48 hours. The mixture was cooled, solid removed by filtration and solvent evaporated. The residual oil was dissolved in methanol and treated with a solution of ether saturated with hydrogen chloride. The precipitated solid was crystallised twice from methanol to give methyl 2-p-(2-[(2-hydroxy-3-phenoxypropyl)amino]ethoxy)phenoxyacetate hydrochloride, 0.22 g, mp 170° C.; microanalysis: found C, 58.2; H, 6.3; N, 3.6; Cl, 8.8%; required for $C_{20}H_{26}NClO_6$: C, 58.3; H, 6.3; N,3.4; Cl, 8.6%; NMR: 3.08 (dd, 1H, CHC$\underline{H}_2$NH), 3.26 (dd, 1H, CHC$\underline{H}_2$NH), 3.36 (t, 2H, NHC$\underline{H}_2$CH$_2$), 3.7 (s,3H, CO$_2$CH$_3$), 4.0 (d,2H, OCH$_2$CH), 4.25(m, 3H, OCH$_2$.-CHOH—), 4.74 (s, 2H, OC$\underline{H}_2$CO), 6.8–7.05 (m, 7 aromatic H), 7.31 (m,2 aromatic H). The hydrochloride (1.9 g) was partitioned between 5% w/v sodium hydrogen carbonate solution (50 ml) and dichloromethane (50 ml). The organic layer was dried (Mg SO$_4$) and the solvent evaporated. The residual solid was crystallised from methanol to give methyl 2-p-(2-[(2-hydroxy-3-phenoxypropyl)amino]-ethoxy)phenoxyacetate (1.67 g). mp 116°–118° C.

The starting propylamine derivative was obtained as follows:

(a) A stirred mixture of 2-(p-hydroxyphenoxy)ethylamine (4.0 g) and benzaldehyde (5.0 g) in methanol (50 ml) was cooled with ice and sodium borohydride (2.0 g) was added in portions over one hour. After stirring for a further 18 hours the solvent was evaporated. The residue was partitioned between 2M hydrochloric acid (200 ml) and ethyl acetate (100 ml).

The acid layer was separated, made alkaline with potassium carbonate and then extracted with ethyl acetate. The extracts were dried (MgSO$_4$) and evaporated. The residual oil was dissolved in ethyl acetate and dry hydrogen chloride was passed through the solution until no further solid precipitated. The precipitate was collected and recrystallised from methanol and ethyl acetate to give N-benzyl-2-(p-hydroxyphenoxy)ethylamine hydrochloride *(2.3 g), mp 182°–184° C.

*The starting N-benzyl-2-(p-hydroxyphenyl)ethylamine hydrochloride may also be obtained as follows: A mixture of p-(2-bromoethoxy)phenol (2.2 g), benzylamine (1.07 g) and triethylamine (1.01 g) in ethanol (30 ml) was heated under reflux for 18 hours. The solvent was evaporated and the residue was partitioned between 2M hydrochloric acid (100 ml) and ethyl acetate (50 ml). The acid layer was separated, made alkaline with potassium carbonate and then extracted with ethyl acetate. The extracts were dried (MgSO$_4$) and the solvent was evaporated. The residual oil was dissolved in ethyl acetate. Dry hydrogen chloride was then passed through the solution until no further solid precipitated. The solid was collected by filtration and recrystallised from a mixture of methanol and ethyl acetate to give N-benzyl-2-(p-hydroxyphenoxy)ethylamine hydrochloride, 0.9 g, mp 182°–184° C.

(b) N-Benzyl-2-(p-hydroxyphenoxy)ethylamine hydrochloride (3.5 g) was shaken with 1M sodium hydroxide solution (20 ml) and dichloromethane (20 ml). The organic layer was separated and washed with water (10 ml), dried (MgSO$_4$) and the solvent evaporated to give N-benzyl-2-(p-hydroxyphenoxy)ethylamine as an oil.

(c) A mixture of N-benzyl-2-(p-hydroxyphenoxy)ethylamine (2.5 g) and 1,2-epoxy-3-phenoxypropane (1.54 g) in propan-2-ol (50 ml) was heated under reflux for 72 hours. The solvent was removed by evaporation to give N-benzyl-N-(2-p-hydroxyphenoxyethyl)-2-hydroxy-3-phenoxypropylamine as an oil which was essentially pure as indicated by thin layer chromatography (TLC) [using silica plates and 5% methanol in dichloromethane as eluant] and was used without purification.

EXAMPLE 2

The procedure described in Example 1 may be repeated using the (—)-enantiomeric form of methyl 2-p-(2-[(2-hydroxy-3-phenoxypropyl)amino]ethoxy)- phenoxyacetate (Z) (0.66 g) to obtain the corresponding optically active form of N-methyl-2-p-(2-[(2-hydroxy-3-phenoxypropyl)amino]ethoxy)phenoxyacetamide (0.50 g), m.p. 114°–116° C.; $^{25}[\alpha]_D = -8.1°$ (C=0.97, ethanol).

The starting material (Z) is available as follows:

A mixture of methyl 2-p-(2-[(2-hydroxy-3-phenoxypropyl)amino]ethoxy)phenoxyacetate, (0.92 g), (−)-di-p-toluoyltartaric acid monohydrate (0.991 g) in methanol (15 ml) was evaporated by boiling to give a final volume of 5 ml. Methyl acetate (10 ml) was added and the mixture was again concentrated to 5 ml volume. This treatment was repeated once more. The mixture was left at ambient temperature for 18 hours. The solid which had formed was collected and crystallised from methanol and methyl acetate to give (−)-methyl 2-p-(2-[(2-hydroxy-3-phenoxypropyl)amino]ethoxy)phenoxyacetate (−)-di-p-toluoyltartrate, (0.337 g); mp 146°–148° C.; $^{25}[\alpha]_D = -80.3°$ (C=0.97; methanol).

(−)-Methyl 2-p-(2-[(2-hydroxy-3-phenoxypropyl)amino]ethoxy)phenoxyacetate (−)-di-p-toluoyltartrate (0.33 g) was partitioned between 5% w/v sodium hydrogen carbonate solution (10 ml) and dichloromethane (10 ml). The organic layer was separated, dried (MgSO₄) and the solvent was evaporated. The residual solid, (0.148 g), mp 114°–116° C., $^{23}[\alpha]_D = -7.8°$ (C=0.97; dichloromethane), was dissolved in methyl acetate. Dry hydrogen chloride gas was passed through the solution until no further solid precipitated. The precipitate was collected and crystallised from methanol and methyl acetate to give (−)-methyl 2-p-(2-[(2-hydroxy-3-phenoxypropyl)amino]ethoxy)phenoxyacetate hydrochloride, (0.092 g), mp 156°–157° C., $^{23}[\alpha]_D = -12.1°$ (C=1.0; methanol).

EXAMPLES 3–16

Using a similar procedure to that described in Example 1 (but using the appropriate amine of the formula H.NR²R³ and carrying out the reaction essentially to completion as judged by thin layer chromatographic [TLC] analysis on silica), there were obtained the following compounds of the formula IX in yields of 60 to 90%, isolated either as the free base or the hydrochloride or oxalate salt by reaction of the free base with ethereal hydrogen chloride or oxalic acid and recrystallisation from the indicated solvents:

| Example | R²R³N— | position of substitution in ring X | mp (°C.) | solvent for recrystallisation |
| --- | --- | --- | --- | --- |
| 3. | dimethylamino | 4 | 84–85 | EtOAc |
| 4. | methylamino | 3 | 184–186°* | MeOH/EtOAc |
| 5. | 2-hydroxyethylamino | 4 | 121–121.5° | MeOAc |
| 6. | benzylamino | 4 | 111–113° | MeOAc |
| 7. | isopropylamino | 4 | 110–111° | MeOAc/hexane |
| 8. | piperidino | 4 | 68–69° | EtOAc |
| 9. | 2-methoxyethylamino | 4 | 96–97° | EtOAc |
| 10. | cyclopentylamino | 4 | 103–104° | EtOAc |
| 11. | pyrrolidino | 4 | 66–67° | EtOAc/hexane |
| 12. | 1,2,3,4-tetrahydroisoquinol-2-yl | 4 | 154–156°* | MeOH/MeOAc |
| 13. | morpholino | 4 | 168–169°** | MeOH |
| 14. | butylamino | 4 | 106–107° | EtOAc |
| 15. | isobutylamino | 4 | 104–105° | EtOAc |
| 16. | propylamino | 4 | 105–106° | EtOAc |

Notes:
*Hydrochloride salt
**Oxalate salt;
MeOH = methanol
MeOAc = methyl acetate
EtOAc = ethyl acetate The starting ester for Example 4 was obtained as follows:

(i) A mixture of resorcinol (88 g), 1,2-dibromoethane (180 g) and potassium hydroxide (44.8 g) was stirred under reflux in methanol (600 ml) for 24 hours. The reaction mixture was cooled. The residual solid was removed by filtration and the filtrate was evaporated to give 3-(2-bromoethoxy)phenol as an oil which was essentially pure as indicated by TLC [using silica plates and 10% v/v methanol in dichloromethane as eluant] and was used without purification.

(ii) A mixture of 3-(2-bromoethoxy)phenol (40 g) and benzylamine (39.2 g) was stirred under reflux in ethanol (800 ml) for 18 hours. The reaction mixture was cooled and the solvent evaporated. The residual oil was dissolved in ethyl acetate (200 ml). The solution was washed with 2M hydrochloric acid (100 ml). The aqueous layer was basified with solid potassium carbonate and extracted with ether (2×100 ml). The extracts were washed successively with water (50 ml) and brine (50 ml), and were then dried (MgSO₄). The dry ethereal solution was treated with a solution of ether saturated with hydrogen chloride.

The precipitated solid was crystallised twice from a mixture of methanol/ethyl acetate to give N-benzyl-2-(m-hydroxyphenoxy)ethylamine hydrochloride (19.2 g), mp 148°–149° C.; NMR: 3.2 (t,2H, CH₂NH), 4.22 (s+t, 4H, CH₂Ph), 6.4 (m,3 aromatic H), 7.1 (t,1 aromatic H), 7.3–7.8 (m,5 aromatic H).

(iii) A mixture of N-benzyl-2-(m-hydroxyphenoxy)ethyl- amine hydrochloride (2.79 g), 1,2-epoxy-3-phenoxypropane (1.5 g) and anhydrous potassium carbonate (2.0 g) was heated under reflux in propan-2-ol for 18 hours. The reaction mixture was cooled and the solvent was evaporated to give N-benzyl-N-(2-m-hydroxyphenoxyethyl)-2-hydroxy-3-phenoxypropylamine as an oil, which was essentially pure as indicated by TLC [using silica plates and 5% methanol in dichloromethane as eluant] and was used without purification.

(iv) N-Benzyl-N-(2-m-hydroxyphenoxyethyl)-2-hydroxy-3-phenoxypropylamine (1.6 g) was reacted with methyl bromoacetate (0.5 g), anhydrous potassium carbonate (0.6 g) and potassium iodide (0.05 g) in acetone (80 ml), using a similar procedure to that described for the starting ester in Ex.1 and with intermediate isolation of methyl 2-m-(2-[N-benzyl-(2-hydroxy-3-phenoxypropyl)amino]ethoxy)phenoxyacetate (1.1 g). There was obtained methyl 2-m-(2-[(2-hydroxy-3-phenoxypropyl)amino]-ethoxy)phenoxyacetate hydrochloride (0.35 g), mp 164°–167° C.; microanalysis, found: C, 58.0; H,6.5; N,3.3; Cl, 8.7%; required for C₂₀H₂₆NClO₆; C, 58.3; H,6.4; N,3.4; Cl, 8.6%; NMR: 3.1 (dd,1H, CHCH₂NH), 3.25 (dd,1H, CHCH₂NH), 3.4 (t,2H, NHCH₂CH₂), 3.7 (s,3H, CO₂CH₃), 3.9–4.1 (m,2H, OCH₂CH), 4.2–4.4 (m,3H, OCH₂.CHOH—), 4.78 (s,2H, OCH₂CO) 5.98 (d,1H, CHOH), 6.5–6.7 (m, 3 aromatic H), 6.9–7.0 (m,3 aromatic H), 7.1–7.4 (m,3 aromatic H), 9.1 (s,2H, NH$_2$+).

EXAMPLES 17–18

Using a similar procedure to that described in Examples 3–16, but starting from methyl 2-p-(2-[(3-o-fluorophenoxy-2-hydroxypropyl)amino]ethoxy)phenoxy-acetate, there were obtained in yields of approximately 80–90%: (Example 17): N-methyl-2-p-(2-[(3-o-fluorophenoxy-2-hydroxypropyl)amino]ethoxy)phenox-yacetamide as its hydrochloride salt, mp 168°–169° C. (recrystallised from methanol/ethyl acetate); and (Example 18): N-piperidino-2-p-(2-[(3-o-fluorophenoxy-2-hydroxypropyl)amino]ethoxy)phenoxyacetamide as its hydrochloride salt, mp 144°–146° C. (recrystallised from ether/methanol).

The required starting methyl ester was obtained as follows:

(i) A mixture of N-benzyl-2-(p-hydroxyphenoxy)ethylamine hydrochloride (see Example 1) (5.6 g), 1,2-epoxy-3-o-fluorophenoxypropane (3.6 g) and anhydrous potassium carbonate (2.7 g) was heated under reflux in propan-2-ol (100 ml) for 24 hours. The reaction mixture was cooled, the solid removed by filtration and the solvent evaporated from the filtrate. The residual oil was purified by chromatography on silica eluting with 1% v/v methanol in dichloromethane to give N-benzyl-N-(2-p-hydroxyphenoxyethyl)-3-o-fluorophenoxy-2-hydroxypropylamine as a colourless oil; NMR: 2.27–3.15 (m, 4H, CH$_2$NCH$_2$), 3.8 (dd,2H, NCH$_2$Ph), 3.9–4.2 (m,5H, OCH$_2$.CHOH, o-F-Ph.OCH$_2$), 6.7 (s, 4 aromatic H), 6.8–7.1 (m, 4 aromatic H), 7.3 (m,5H, CH$_2$Ph).

(ii) A mixture of N-benzyl-N-(2-p-hydroxyphenoxyethyl)-3-o-fluorophenoxy-2-hydroxypropylamine (5.4 g), methyl bromoacetate (2.0 g), anhydrous potassium carbonate (1.79) and potassium iodide (0.05 g) was stirred under reflux in dry acetone (80 ml) for 24 hours. The reaction mixture was cooled, solid removed by filtration and the solvent evaporated. The residue was dissolved in dichloromethane (40 ml) and washed successively with 10% w/v sodium bicarbonate solution (20 ml) and water (20 ml), then dried (MgSO$_4$) and the solvent removed by evaporation. The oil (6.18 g) obtained was purified by chromatography on silica, eluting with 1% v/v methanol in dichloromethane to give methyl 2-p-(2-[N-benzyl-(3-o-fluorophenoxy-2-hydroxypropyl)amino]ethoxy)phenoxyacetate as a colourless oil. This was dissolved in methanol (100 ml) and stirred with decolourising charcoal (1 g) for 1 hour. The charcoal was removed by filtration and the filtrate was hydrogenated in the presence of benzyl chloride (0.71 g) and 10% w/w palladium-on-carbon for 2 hours at atmospheric pressure. The catalyst was removed by filtration and the solvent was evaporated from the filtrate. The residual solid was crystallised twice from a mixture of methanol and anhydrous ether to give methyl 2-p-(2-[(3-o-fluorophenoxy-2-hydroxypropyl)amino]ethoxy)-phenoxyacetate hydrochloride (0.55 g), mp 120°–122° C.; microanalysis, found: C,55.7; H,5.9; N,3.2; Cl,8.3%; required for C$_{20}$H$_{25}$NClFO$_6$: C,55.9; H,5.9; N,3.3; Cl, 8.2%; NMR: 3.1 (dd, 1H, CHCH$_2$NH), 3.27 (m under HOD peak, 1H, CH.CH$_2$NH), 3.41 (t,2H, NHCH$_2$CH$_2$), 3.68 (s,3H, CO$_2$CH$_3$), 4.05 (d, 2H, OCH$_2$CH), 4.25 (d+m, 3H, OCH$_2$, CHOH), 4.71, (s, 2H, OCH$_2$CO), 5.93 (d,1H, CHOH), 6.8–7.0 (m, 5 aromatic H), 7.1–7.3 (m, 3 aromatic H), 9.12 (broad s, 2H, NH$_2$+).

EXAMPLE 19

Using a similar procedure to that described in Example 2, the (−)-enantiomeric phenoxyacetate (Z) (0.6 g) was converted to N-(2-hydroxyethyl)-2-p-(2-[(2-hydroxy-3-phenoxypropyl)amino]ethoxy)phenox-yacetamide (0.32 g), mp 111°–113° C., $^{25}[\alpha]_D = -7.1°$ (C=0.99; ethanol), using ethanolamine in place of methylamine.

EXAMPLES 20–27

Using a similar procedure to that described in Example 1 (but using the appropriate amine of the formula H.NR$^2$R$^3$ and carrying out the reaction essentially to completion as judged by TCL analysis on silica), the following compounds of the formula IX (substituent-−OCH$_2$CO.NR$^2$R$^3$ located in position 4 of ring X) were obtained in yields of 55 to 85%, isolated as the free bases and after recrystallisation from the indicated solvents:

| Example | R$^2$R$^3$N— | mp (°C.) | solvent for recrystallisation |
|---|---|---|---|
| 20 | ethylamino | 104–105 | EtOAc |
| 21 | allylamino | 97–98 | EtOAc |
| 22 | 2-phenylethylamino | 134–135 | MeOH |
| 23 | 4-chlorobenzylamino | 126–127 | MeOH |
| 24 | 3-hydroxypropylamino | 103–104 | MeOH/EtOAc |
| 25 | 3-methoxypropylamino | 88–89 | EtOAc |
| 26 | (carbamoylmethyl)amino | 208–209 | MeOH |
| 27 | 1-phenylethylamino | 132–133 | EtOAc |

EXAMPLE 28

Sodium hydride (0.132 g of a 60% w/w suspension in mineral oil) was added to p-(2-[2-hydroxy-3-phenoxypropylamino]-ethoxy)phenol (1.0 g) dissolved in dry dimethylformamide (DMF) (50 ml). The resulting suspension was stirred for approximately 30 minutes until a clear solution was obtained. A solution of N-phenyl-2-chloroacetamide (0.559 g) in dry DMF (20 ml) was added and the mixture was stirred for 18 hours. It was then poured into water (150 ml). The mixture obtained was extracted with dichloromethane (2×100 ml). The extracts were washed with water (6×100 ml), then dried (MgSO$_4$) and the solvent evaporated. The residue was crystallised from ethyl acetate to give N-phenyl-2-p-(2-[(2-hydroxy-3-phenoxypropyl)amino]ethoxy)-phenoxyacetamide (0.365 g), mp 119°–121° C.; microanalysis: found C,68.7; H, 6.5; N, 6.3; required for C$_{25}$H$_{28}$N$_2$O$_5$: C, 68.8; H 6.4; N, 6.4%; and having a satisfactory NMR spectrum.

The starting phenol was obtained as follows:

(i) A mixture of p-(2-aminoethoxy)phenol hydrochloride (1.89 g) triethylamine (1.01 g) and 1,2-epoxy-3-phenoxypropane (1.5 g) was heated under reflux for 24 hours. The reaction mixture was cooled and the solvent was evaporated. The residue was partitioned between dichloromethane (100 ml) and 10% w/v potassium carbonate solution. The organic layer was separated, dried (MgSO$_4$), and the solvent was evaporated. The residual oil was dissolved in ethyl acetate and dry hydrogen chloride was passed through the solution until no further solid precipitated. The precipitate was collected and recrystallised from methanol and ethyl acetate to give p-(2-[2-hydroxy-3-phenoxypropylamino]-ethoxy)phenol hydrochloride (0.53 g), mp, 171°–72° C.; microanalysis: found C,60.3; H,6.7; N,4.0; Cl, 10.6%;

required for $C_{17}H_{22}NClO_4$: C,60.1; H,6.5; N,4.1; Cl,10.5%.

(ii) The hydrochloride salt (1.5 g), obtained by procedure (i), was partitioned between 5% w/v aqueous sodium hydrogen carbonate solution (15 ml) and dichloromethane (15 ml). The organic phase was separated, dried (MgSO$_4$) and the solvent was removed by evaporation to give p-(2-[2-hydroxy-3-phenoxypropylamino]ethoxy)phenol as a stiff syrup (1.1 g), which was used without further purification.

N-Phenyl-2-chloroacetamide was obtained as follows:

A mixture of aniline (9.3 g) and triethylamine (10.1 g) in dichloromethane (40 ml) was added dropwise during 1 hour to an ice-cooled solution of chloroacetyl chloride (11.3 g) in dichloromethane (40 ml). The mixture was further stirred for 18 hours. The organic phase was separated by filtration, washed with water (3×50 ml), dried (MgSO$_4$) and the solvent removed by evaporation to give N-phenyl-2-chloroacetamide (6.1 g) as a white solid, mp 128°–129° C., which was used without further purification.

EXAMPLE 29

Using an analogous procedure to that described in Example 28, but using N-propyl-2-chloroacetamide (0.447 g) in place of N-phenyl-2-chloroacetamide, there was obtained N-propyl-2-p-(2-[2-[(2-hydroxy-3-phenoxypropyl)amino]ethoxy)phenoxyacetamide (0.47 g), mp 105°–107° C. (recrystallised from ethyl acetate), essentially identical in all respects to the material obtained in Example 16.

The starting N-propyl-2-chloroacetamide was obtained in an analogous manner to that for N-phenyl-2-chloroacetamide i.e. by reacting propylamine with chloroacetyl chloride. It was obtained as an oil which was used without special purification.

EXAMPLE 30

(−)-Methyl 4-[2-(2-hydroxy-3-phenoxypropylamino)ethoxy]phenoxyacetate (44.0 g) (the same starting material as in Example 2) and 2-methoxyethylamine (30 ml) were heated together on a steam-bath for 24 hours. The mixture was cooled and evaporated under reduced pressure to give an oily residue. This was dissolved in dichloromethane (200 ml) and treated with a solution of ether saturated with hydrogen chloride. The solvent was evaporated and the residual solid crystallised from a mixture of methanol and ethyl acetate to give (S)-4-[2-(2-hydroxy-3-phenoxypropylamino)ethoxy]-N-(2-methoxyethyl)phenoxyacetamide hydrochloride (39.2 g), m.p. 171°–3° C.; $\alpha_D = -10.7°$ (c=1.0; methanol); microanalysis: found C, 58.1; H, 7.0; N, 6.0; Cl, 7.9%; required for $C_{22}H_{31}ClN_2O_6$: C, 58.1; H, 6.9; N, 6.2; Cl 7.8%: NMR (DMSO-d$_6$) 3.1(m,1H, CHCH$_2$NH); 3.24(s,3H,OCH$_3$); 3.24–3.45(m,7H,CHCH$_2$NHCH$_2$; NHCH$_2$CH$_2$OCH$_3$); 4.0(m,2H, ArOCH$_2$CHOH); 4.2–4.35(m,3H,CHOH; CH$_2$CH$_2$OAr); 5.95(d,1H,OH); 6.85–7.05(m,7H,Ar); 7.3(m,2H,Ar); 8.15(t,1H, CONHCH$_2$); 9.16 and 9.35 (broad peaks, 2H, NH$_2$+).

EXAMPLE 31

As stated previously, suitable pharmaceutical compositions of compounds of formula I defined hereinbefore may be obtained by standard formulation techniques.

A typical tablet formulation suitable for oral administration to warm-blooded animals comprises as active ingredient a micronised form of a compound of formula I, or a pharmaceutically acceptable salt thereof, as defined hereinbefore (for example as described in one of the preceding Examples), and may be produced by direct compression together with micronised lactose containing a standard disintegrant and/or lubricant. When tablets containing small amounts of active ingredient (for example 0.5–10 mg) are required, the active ingredient may be micronised together with lactose in the ratio of 1:10 parts by weight and then this material is diluted with further lactose or microcrystalline cellulose containing 0.5% by weight of a lubricant (such as magnesium stearate) and 5% by weight of a disintegrant (such as cross-linked sodium carboxymethyl cellulose or sodium starch glycolate).

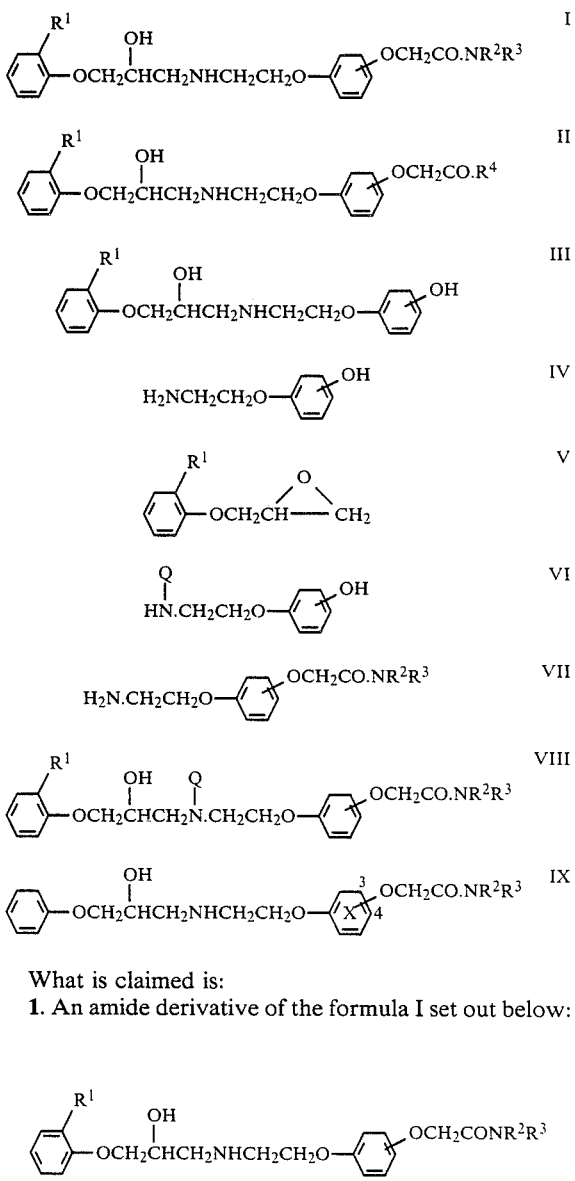

What is claimed is:

1. An amide derivative of the formula I set out below:

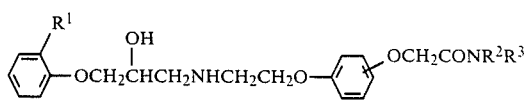

wherein R$^1$ is hydrogen or fluoro; R$^2$ is phenyl optionally bearing a substituent selected from the group consisting of halogeno, (1-4C)alkyl, (1-4C)alkoxy, trifluoromethyl, and nitro, (3-6C)cycloalkyl, (1-4C)alkyl in which the carbon atom linked to the nitrogen of NR$^2$R$^3$ bears one or two hydrogens, or is (3-4C)alkenyl, either of which latter groups may optionally bear a substituent selected from the group consisting of hydroxy, (1-4C-)alkoxy, phenyl and chlorophenyl; and $R^3$ is hydrogen, methyl or ethyl; or a pharmaceutically acceptable acid-addition salt thereof.

2. A compound as claimed in claim 1 wherein $R^2$ is phenyl optionally bearing a substituent selected from the group consisting of fluoro, chloro, bromo, methoxy, ethoxy, methyl, ethyl, trifluoromethyl, and nitro substituents; cyclobutyl, cyclopentyl or cyclohexyl; or $R^2$ is methyl, ethyl, propyl, isopropyl, butyl, isobutyl, allyl or 2-methyl-2-propenyl, optionally bearing a substituent selected from the group consisting of hydroxy, methoxy, ethoxy, phenyl and p-chlorophenyl.

3. A compound as claimed in claim 1 wherein the group $NR^2R^3$ is selected from the group consisting of anilino, allylamino, cyclohexylamino, cyclopentylamino, dimethylamino, diethylamino, methylamino, ethylamino, propylamino, isopropylamino, butylamino, isobutylamino, (2-hydroxyethyl)amino, (3-hydroxypropyl)amino and (2-methoxyethyl)amino.

4. A compound as claimed in claim 1 wherein the the groups —OCH$_2$.CO.NR$^2$R$^3$ and —O.CH$_2$CH$_2$.NH— are attached in para relationship.

5. A compound of the formula I as depicted in claim 1 wherein $R^1$ is hydrogen; the group $NR^2R^3$ selected from (3-4C)alkenylamino, and (1-4C)alkylamino, in which latter group the carbon atom linked to the nitrogen bears one or two hydrogens; and the groups —OCH$_2$.CO.NR$^2$R$^3$ and —O.CH$_2$CH$_2$.NH— are attached in para-relationship; or a pharmaceutically acceptable acid-addition salt thereof.

6. A compound of the formula I as depicted in claim 1 wherein $R^1$ is hydrogen; the group —NR$^2$R$^3$ is selected from methylamino, ethylamino, propylamino, isopropylamino, (2-hydroxyethyl)amino, (3-hydroxypropyl)amino, (2-methoxyethyl)amino and (3-methoxypropylamino; and the groups —OCH$_2$.CO.NR$^2$R$^3$ and —O.CH$_2$CH$_2$.NH— are attached in para-relationship; or a pharmaceutically acceptable acid-addition salt thereof.

7. A compound selected from the group consisting of N-methyl-, N-propyl-, N-(2-hydroxyethyl)- and N-allyl-2-p-(2-[(2-hydroxy-3-phenoxypropyl)amino]ethoxy)phenoxyacetamide, and the pharmaceutically acceptable acid-addition salts thereof.

8. The laevotatory optically active form of N-methyl-2-p-(2-[(2-hydroxy-3-phenoxypropyl)amino]ethoxy)-phenoxyacetamide or a pharmaceutically acceptable acid-addition salt thereof.

9. 4-[2-(2-Hydroxy-3-phenoxypropylamino)ethoxy]-N-(2-methoxyethyl)phenoxyacetamide or a pharmaceutically acceptable acid addition salt thereof.

10. (S)-4-[2-(2-Hydroxy-3-phenoxypropylamino)ethoxy]-N-(2-methoxyethyl)phenoxyacetamide or a pharmaceutically acceptable acid addition salt thereof.

11. (S)-4-[2-(2-Hydroxy-3-phenoxypropylamino)ethoxy]-N-(2-methoxyethyl)phenoxyacetamide hydrochloride.

12. A salt as claimed in claim 1 which is with an inorganic or organic acid affording a pharmaceutically acceptable anion.

13. A thermogenic pharmaceutical composition comprising a thermogenically effective amount of a compound of the formula I, or of a pharmaceutically acceptable acid-addition salt thereof, as defined in claim 1, together with a pharmaceutically acceptable diluent or carrier.

14. A method for producing a thermogenic effect in a warm-blooded animal requiring such treatment which comprises administering to said animal a thermogenically effective amount of a compound of the formula I, or of a pharmaceutically acceptable acid-addition salt thereof, as defined in claim 1.

* * * * *